United States Patent [19]

Burrington et al.

[11] Patent Number: 4,519,954

[45] Date of Patent: May 28, 1985

[54] LEACH RESISTANT CATALYST USEFUL FOR THE DIMERIZATION OF ACRYLIC COMPOUNDS

[75] Inventors: James D. Burrington, Richmond Hts.; Fred A. Pesa, Aurora; Elizabeth A. Maher, University Hts.; Robert K. Grasselli, Chagrin Falls, all of Ohio

[73] Assignee: The Standard Oil Company, Cleveland, Ohio

[21] Appl. No.: 454,508

[22] Filed: Dec. 29, 1982

[51] Int. Cl.$^3$ .................. C07C 121/20; C07C 121/26; C07C 55/14; C07C 57/13; C07C 13

[52] U.S. Cl. ............................ 260/465.8 D; 502/154; 502/162; 502/167; 502/168; 502/171; 560/202; 562/590; 562/595; 564/160; 568/461; 568/463

[58] Field of Search ................ 260/465.8 D; 564/160; 568/463, 461; 562/590, 595; 560/202

[56] References Cited

U.S. PATENT DOCUMENTS

| | | | |
|---|---|---|---|
| 3,484,475 | 12/1969 | Cornforth et al. | 260/465.8 D |
| 3,655,724 | 4/1972 | Linn et al. | 260/465.8 D |
| 3,790,617 | 2/1974 | Masada et al. | 260/465.8 D |
| 3,907,852 | 9/1975 | Oswald et al. | 260/448.2 N |
| 3,946,066 | 3/1976 | Todd | 260/465.8 D |
| 3,968,147 | 7/1976 | Solodar | 502/162 X |
| 3,972,953 | 8/1976 | Lyons | 502/162 X |
| 3,981,900 | 9/1976 | Chabardes et al. | 260/465.8 D |
| 4,024,193 | 5/1977 | Kruse | 502/162 X |
| 4,089,890 | 5/1978 | Jennings et al. | 260/465.8 D |
| 4,169,853 | 10/1979 | Knifton | 502/162 X |
| 4,333,852 | 6/1982 | Warren | 502/162 |
| 4,384,981 | 5/1983 | Dines et al. | 502/162 X |
| 4,422,980 | 12/1983 | Grasselli et al. | 260/465.8 D |

OTHER PUBLICATIONS

Ugo, "Aspects of Homogeneous Catalysis", (1974), pp. 175–180, Reidel Pub. Co., Boston–U.S.A./Dordrecht–Holland.

*Primary Examiner*—Joseph Paul Brust
*Attorney, Agent, or Firm*—Teresan W. Gilbert; Joseph G. Curatolo; Larry W. Evans

[57] ABSTRACT

A catalyst and a liquid phase process are provided for the dimerization of acrylic compounds. The process includes contacting an acrylic compound with the catalyst in the presence of hydrogen, wherein the catalyst comprises an inorganic oxide catalyst support, trivalent pendant atoms covalently bonded to the support and ruthenium complexed with said trivalent pendant atoms.

22 Claims, No Drawings

LEACH RESISTANT CATALYST USEFUL FOR THE DIMERIZATION OF ACRYLIC COMPOUNDS

BACKGROUND OF THE INVENTION

The present invention relates to the liquid phase dimerization of an acrylic compound to form the corresponding dimer. More specifically, this invention relates to the dimerization of acrylic compounds by contacting an acrylic compound with a ruthenium based catalyst in the presence of hydrogen, at a pressure of least about 1 psi and a temperature of at least about 50° C., wherein the catalyst comprises an inorganic oxide catalyst support, trivalent pendant atoms covalently bonded to the support and ruthenium complexed with said trivalent pendant atoms.

It has long been known that the dimerization of acrylic compounds may be catalyzed by ruthenium based catalysts. It is also known in the art that these catalysts may be disposed on a variety of support materials, such as organic polymers and inorganic oxides.

U.S. Pat. No. 3,790,617 to Masada, et al. discloses a process for the dimerization of organic nitriles by contacting them with hydrogen in the presence of a ruthenium catalyst. This catalyst may be prepared by disposing a ruthenium compound, such as $RuCl_3$, onto a support material, such as active carbon, alumina, silica, diatomaceous earth and pumice. The catalyst may also be promoted by adding promoting compounds, such as an organophosphorus, to the supported catalyst.

U.S. Pat. No. 3,655,724 to Linn, et al. also discloses a process for the dimerization of acrylic compounds by contacting the acrylic compound with hydrogen in the presence of a ruthenium catalyst. This catalyst is prepared by reacting a water soluble ruthenium salt with an aqueous solution of a carboxylic acid to form a ruthenium-acid complex which is absorbed onto a support of charcoal or n-alumina.

Although ruthenium has long been known as a dimerization catalyst, previous processes suffered from the limitation of using catalysts which showed poor stability. These catalysts also often were homogeneous with respect to the reaction mixture, making separation of the catalyst from the reaction mixture difficult and costly.

Recycling of the catalyst is often desirable because the catalyst often accounts for a major portion of the cost of a process. In fact, recycling of the catalyst may be necessary to make a process cost effective. This is particularly true for ruthenium based catalysts due to the relatively high cost of ruthenium metal. In previous processes, however, efficient catalyst recycling is often impractical due to difficulties in separating the catalyst from the reaction mixture. Previous heterogeneous catalysts also suffer from the limitation of readily leaching ruthenium to the reaction medium. This makes catalyst recycling impracticable and increases the process cost over what the cost would most likely be if the catalyst could be recycled.

SUMMARY OF THE INVENTION

It is therefore an object of the present invention to provide a catalyst wherein the catalyst is leach resistant for ruthenium, and to provide a process for the dimerization of acrylic compounds by contacting an acrylic compound with a catalyst in the presence of hydrogen wherein the catalyst is leach resistant for ruthenium.

It is a further object of the present invention to provide a catalyst which shows good conversion and selectivity for the dimer, and to provide a process for the dimerization of acrylic compounds by contacting an acrylic compound, in the presence of hydrogen, with a catalyst which shows good conversion and selectivity for the dimer.

These and other objects and advantages of the present invention are described in and become apparent from the specification which folllows. The above and other objects and advantages are accomplished by the invention as hereinafter described and claimed.

In general the present invention includes a liquid phase process for the dimerization of acrylic compounds comprising contacting an acrylic compound with a ruthenium based catalyst in the presence of hydrogen, at a pressure of least about 1 psi and a temperature of at least about 50° C., wherein the catalyst comprises an inorganic oxide catalyst support, trivalent pendant atoms covalently bonded to the support and ruthenium complexed with said trivalent pendant atoms. The present invention is also directed to the catalyst described above.

DETAILED DESCRIPTION OF THE INVENTION

Acrylic compounds may be defined as carboxyl or nitrile containing organic compounds which have a double bond in a position "alpha" to the nitrile or carboxyl group. These compounds may be dimerized by the process of the present invention to form the corresponding dimers. Examples of compounds suitable for the present invention and their corrresponding dimers are listed below in Table I. Other suitable acrylic compounds may include acrylic acid, methacrylic acid and the acrylates, such methyl acrylate, ethyl acrylate, and methyl methacrylate. This process is, however, especially preferred for the dimerization of acrylonitrile.

TABLE I

| Acrylic Compound | Dimer |
|---|---|
| acrylonitrile | dicyanobutene |
|  | adiponitrile |
| methacrylonitrile | 2,4-dimethyl-dicyanobutene |
|  | 2,4-dimethyl-dicyanobutane |
| acrylamide | adipamide |
|  | 2,3-dihydromuconamide |
| methacrylamide | 2,4-dimethyl-adipamide |
|  | 2,4-dimethyl-2,3-dihydromuconamide |
| acrolein | adipaldehyde |
|  | 2,3-dihydromuconaldehyde |
| methacrolein | 2,5-dimethyl-adipaldehyde |
|  | 2,5-dimethyl-2,3-dihydromuconaldehyde |

These dimers have several uses, including that of being precursers for the formation of nylons and other polymers. For example, the dimerization of acrylonitrile by the process of the present invention yields the linear dimers 1,4-dicyanobutane (adiponitrile) and 1,4-dicyanobutene, useful in making nylon 6,6.

According to the present invention, an acrylic compound is contacted in the liquid phase with a ruthenium based catalyst in the presence of hydrogen. A wide variety of ruthenium complexes are suitable for the catalyst and process of the present invention. These Ru complexes must be capable of catalyzing the dimerization reaction and of being disposed on an inorganic oxide catalyst support. In general these complexes include Ru complexes containing at least two complexing ligands which together have a total of at least four ligating bonds bonding to the ruthenium and are not covalently bonded to the support. Preferably these ligands are selected from the group consisting of halides, such as F, Cl, Br and I; water, carboxylic acids, such as acrylic acid, methacrylic acid, acetic acid and benzoic acid; aliphatic or aromatic carboxylic acid esters, such as benzyl acetate, methyl methacrylate, methacrylate and ethyl acetate; alcohols, such as methanol and ethanol; nitriles, such as acrylonitrile, acetonitrile and benzonitrile; aldehydes, such as acrolein and methacrolein; amides, such as acrylamide and glycols, such as ethylene glycol, or their derivatives; phosphines, such as triphenylphosphine; arsines, such as triphenylarsine and amines, such as triethylamine and ammonia, or mixtures thereof.

More preferably, however, the ruthenium is in the form of a complex represented by the formula:

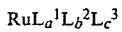

wherein $L^1$ is a mono or bidentate ligand selected from F, Cl, Br, I, 2,4-pentanedionate, or mixtures thereof, wherein $L^2$ is one or more of acrylonitrile, methacrylonitrile, acetonitrile, propionitrile, benzonitrile, water and a group of the formula:

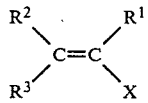

wherein X is CN, $CO_2R^4$, CHO or $CONR_2^4$ and $R^1$, $R^2$, $R^3$ and $R^4$ are independently selected from $C_{1-16}$ alkyl, $C_{6-16}$ aryl and H,
wherein $L^3$ is $R_3^5P$, $R_3^5As$, $R_3^5Sb$, $R_3^6N$, $R_3^5Bi$, $R_2^6S$ and $R_2^6O$, or mixtures thereof wherein each $R^5$ is a $C_{1-16}$ group independently selected from alkyl, aryl, alkoxy, aryloxy, dialkylamino and diarylamino and $R^6$ is independently selected from $C_{1-16}$ alkyl, $C_{6-16}$ aryl or H, and further
wherein
  a is 0 to 3;
  b is 0 to 6;
  c is 0 to 6; and
  a + b + c is at least 2 additionally and further selected so that $L^1$, $L^2$ and $L^3$ are additively bonded to the Ru with 4 to 6 ligating bonds.

Suitable Ru complexes include $RuCl_3 \cdot 3H_2O$, Ru(acac)$_3$, $RuCl_2(AN)_3$, $RuBr_2(AN)_3$, $Ru(I)_2(AN)_3$, $RuCl_2(AN)_4$, $RuCl_2(CH_3CN)_3$, $RuCl_2$(propionitrile)$_3$, $RuCl_2(PhCN)_4$, $RuBr_2(AN)_4$, $RuI_2(AN)_4$, $RuCl_2(C_{12}H_{18})$, $RuCl_2(C_4H_8)_3$, $RuCl_2(C_8H_{12})_2$, $RuCl_2(C_8H_{12})$(p-toluidine), Ru(stearate)$_3$, Ru(trifluoroacetylacetonate)$_3$, $RuCl_3(AsPh_3)_2$, $RuCl_2(SbPh_3)_4$, $[Ru(NH_3)_5Br]Br_2$ and $[Ru(NH_3)_5I]I_2$, wherein "acac" is 2,4-pentanedionate, "AN" is acrylonitrile, and "Ph" is phenyl. $RuCl_3 \cdot 3H_2O$, Ru(acac)$_3$, $RuCl_2(AN)_3$, $RuBr_2(AN)_3$, $Ru(I)_2(AN)_3$ are, however, especially preferred.

Ruthenium complexes suitable for use in the present invention are available commercially or may be prepared by procedures known in the art. Known procedures for producing suitable ruthenium complexes include refluxing a ruthenium hydrate with a ligand sought to be included in the ruthenium complex. For example, $RuCl_2(AN)_3$ may be prepared by refluxing $RuCl_3 \cdot 3H_2O$ and acrylonitrile in ethanol.

The amount of ruthenium present in the process may vary widely. This amount, however, should be sufficiently great to catalyze the dimerization reaction. For this reason it is preferred that the Ru/acrylic compound molar ratio be at least about $10^{31\ 4}$:1 and more preferably at least about $4 \times 10^{-4}$:1. Optimum conversion and economies are achieved at Ru/acrylic compound molar ratios of about $10^{-4}$:1 to 1:1, and more preferably about $4 \times 10^{-4}$:1 to $2 \times 10^{-3}$:1.

Although, consistent with the present invention, any amount of Ru may be present which can be deposited onto the inorganic oxide catalyst support, it is preferred that the catalyst be about 0.1 to 10 weight percent ruthenium. More preferably the catalyst is about 0.3 to 3 weight percent ruthenium.

The catalyst of the present invention comprises a catalyst support, trivalent pendant atoms covalently bonded to the support and ruthenium complexed with the trivalent pendant atoms. It is critical to the present invention that this support be an inorganic oxide; therefore supports of organic polymers are inherently unsuitable. Inorganic oxides useful in the present invention should be ones which are solids under the process conditions and which are relatively stable under the dimerization reaction conditions. Inorganic oxides useful in the present invention include $Li_2O$, BeO, $MgO_2$, $CaO_2$, $BaO_2$, $Y_2O_3$, $TiO_2$, $ZrO_2$, $HfO_2$, $NbO_2$, $Ta_2O_5$, $WO_2$, ZnO, CdO, $Al_2O_3$, $Ga_2O_3$, $In_2O_3$, $Tl_2O_3$, $SiO_2$, $GeO_2$, $SnO_2$, $Pb_2O$, $Pb_2O_3$, $As_2O_5$, $CeO_2$, $Ce_2O_3$ and $ThO_2$, and mixtures thereof.

It is preferred that the inorganic oxide be one which is capable of forming a strong covalent bond with the trivalent pendant atom moeity. It is also preferred that the inorganic oxide be one which does not act as an oxidizing agent under the process conditions. For this reason it is preferred that the oxide not be an oxide of a transition metal. Preferably, the inorganic oxide comprises an inorganic oxide of an element selected from Group IA, IIA, IIIA, IVA, IIIB, IVB and mixtures thereof, excluding carbon and hydrogen. Preferred inorganic oxides include oxides such as $Li_2O$, $Cs_2O$, BeO, $MgO_2$, $CaO_2$, $BaO_2$, $Al_2O_3$, $Ga_2O_3$, $In_2O_3$, $Tl_2O_3$, $SiO_2$, $GeO_2$, $SnO_2$, $Pb_2O$, $Pb_2O_3$, $TiO_2$, $ZrO_2$, $HfO_2$, $NbO_2$, $Ta_2O_5$ and mixtures thereof.

More preferably the inorganic oxide comprises an inorganic oxide of an element selected from Group IIIA, IVA, IIIB, IVB and mixtures thereof, excluding carbon. These oxides include oxides such as $Al_2O_3$, $Ga_2O_3$, $In_2O_3$, $Tl_2O_3$, $SiO_2$, $GeO_2$, $SnO_2$, $Pb_2O$, $Pb_2O_3$, $TiO_2$, $ZrO_2$, $HfO_2$, $Y_2O_3$ and mixtures thereof.

Most preferably, however, the inorganic oxide comprises an inorganic oxide of an element selected from Group IIIA and IVA and mixtures thereof, such as $Al_2O_3$, $Ga_2O_3$, $In_2O_3$, $Tl_2O_3$, $SiO_2$, $GeO_2$, $SnO_2$, $Pb_2O$ and $Pb_2O_3$ and mixtures thereof. The inorganic oxides $SiO_2$, $TiO_2$, $Al_2O_3$ and mixtures thereof are particularly preferred due to their stability and relatively low cost.

The chemical Groups listed herein are determined in reference to THE HANDBOOK OF CHEMISTRY AND PHYSICS, 61st Edition, 1980-81, CRC Press, Inc., Boca Raton, Fla.

According to the present invention, the inorganic oxide catalyst support is covalently bonded to trivalent pendant atoms. At least some of these trivalent pendant atoms covalently bonded to the inorganic oxide support complex with the ruthenium to strongly bond the ruthenium to the support.

The inorganic oxide/trivalent pendant atom ligating system, and especially the $SiO_2/P$ ligating system, displays exceptional stability and ruthenium bonding power, thereby strongly and stably binding the ruthenium to the support. This diminishes the tendency of Ru to be leached from the support and prolongs the potential life of the ruthenium catalyst and the catalyst's potential for recycling.

In addition, the formation of this inorganic oxide/trivalent pendant atom/ruthenium complex exerts an activating effect on the ruthenium over the activity it possesses when complexed with trivalent atoms not covalently bonded to an inorganic oxide support or when the ruthenium is disposed on an inorganic oxide catalyst support without being complexed with trivalent pendant atoms. To this end, the pendant atoms should be capable of forming strong coordinate bonds with the ruthenium complex. P, As, Sb, Bi and N, when in the trivalent state, are preferred for this purpose. Phosphorus, however, is especially preferred. Mixtures of different pendant atoms may also be used.

As is appreciated by those skilled in the art, trivalent atoms, in order to be trivalent, must be bonded to other groups in addition to the substrate. The nature of these groups is not critical to the invention and may be alkyl, such as methyl or ethyl; aryl, such as phenyl; alkoxy, such methoxy or ethoxy; aryloxy, such as phenoxy; dialkylamino, such as dimethylamino; diarylamino, such as diphenylamino; and hydrogen. Although not necessary for the present invention, it is preferred that these groups contain no more than 12 carbon atoms.

Further, the trivalent pendant atoms are bonded to the inorganic oxide catalyst support through the bonding of hydroxy groups on the surface of the support with the trivalent pendant atom moeity. Therefore, at least one of the groups attached to the trivalent atom will be chosen so as to be suitable for reaction with a hydroxy group on the support to form a covalent bond. Appropriate choices are known in the art or may be readily determined. For example, phosphine groups may be bonded to silica or alumina by reaction of a surface hydroxy group with $(EtO)_3SiCH_2CH_2PPh_2$, wherein "Et" is ethyl and "Ph" is phenyl.

Although sufficient amounts of catalyst should be present in the reaction mixture to provide good conversion of the acrylic compound, it is preferred that the molar ratio of the trivalent pendant atoms to the ruthenium in the catalyst not be greater than 20:1. It has been found that, in general, trivalent pendant atom/ruthenium ratios substantially in excess of 20:1 cause the catalyst to display diminished activity. It is further preferred that the trivalent pendant atom/ruthenium ratio be no greater than 10:1. However, in order to minimize alternative bonding patterns, it is preferred that the trivalent pendant atom/ruthenium ratio be at least 1:1.

When the pendant atoms are phosphorus it is preferred that the amount and distribution of phosphorus atoms in the inorganic oxide be such that the ruthenium atoms of the complex will not bond to two or more pendant phosphorus groups. Consequently, it is preferred that the pendant atoms be randomly distributed in the inorganic oxide at no more than 15 mole percent, and more preferably from 0.1 to 14 and even more preferably from 0.5 to 7 mole percent, based on the total number of monomeric oxide units in the inorganic oxide.

The catalyst may be prepared using any of several known techniques. These techniques include mixing the support with an excess of the Ru complex for a suitable period of time. Preferably this is performed in an inert atmosphere, and, if desired, in a suitable solvent such as a ketone, alcohol or aromatic compound. A preferred technique includes adding the ruthenium complex to the support, either in batches or continuously, over an extended period of time.

The present invention also includes the possibility of the catalyst being promoted with one or more substances. It is preferred that the promoter be a base of Group VA, but the present invention is not limited to Group VA containing bases. When the promoter is a base, it is preferred that this base be on with a $pK_b$ of 0 to about 12. Bases suitable for this purpose include compounds such as N-methylpyrrolidine, triethylamine, sodium phenoxide, sodium carbonate, sodium cyanide, sodium thiophenol, and their potassium and cesium analogs. Organic bases such as N-methylpyrrolidine and triethylamine are, however, preferred. The molar ratio of base promoter to ruthenium should be maintained at 2:1 or more, and preferably at about 5 to about 50.

The process of the present invention may optionally be performed in the presence of any of several known solvents. Suitable solvents include ketones, alcohols, alkyl substituted or unsubstituted aromatics, ethers, organic nitriles and mixtures thereof. Acetone, methyl ethyl ketone, toluene, tetrahydrofuran, ethanol, and acetonitrile are, however, preferred. Dimethyl sulfoxide (DMSO) is not generally preferred as a solvent because its presence as a solvent tends to decrease catalyst effectiveness. In the situation where the reaction is not intended to go to equilibrium, products of the dimerization process may be used in the place of solvents. Excess amounts of the acrylic feeds may, however, be used instead of solvents, consistent with the present invention. The present invention may also be performed in the absence of a solvent or in the absence of an excess amount of a reactant or product.

The process of the present invention is carried out by contacting the acrylic compound with the catalyst for a suitable period of time. This time is determined by various factors, including the identity of the acrylic compound, the quantity of catalyst used and its composition, the temperature and pressure. The appropriate reaction time for a given set of conditions may readily be determined by one skilled in the art.

Usually the reaction is carried out at a temperature of about 50°–400° C. More preferably, however, this temperature is about 60°–200° C., and most preferably about 80°–150° C.

As is appreciated by those skilled in the art, hydrogen must be present in the reaction system. The pressure of the reaction system, exerted by hydrogen, is not critical to the present invention and may vary widely, with pressures on the order of about 1 to 1500 psi and preferably about 10 to 800 psi being suitable. Pressures of about 60–400 psi, however, are most preferred.

It is important to note that the process of the present invention may be practiced as either a batch or continuous process. The stability and leach resistance of the catalyst, however, makes it particularly suited for use in a continuous process.

Due to the fact that the process of the present invention utilizes a catalyst which is heterogeneous to the reaction mixture, catalyst separation and recovery may be by conventional mechanical means, such as filtering, centrifugation or the like. Recovered catalyst may then be reprocessed or directly recycled, as is appropriate. The products may similarly be separated by conventional means, such as distillation or vacuum evaporation.

SPECIFIC EMBODIMENTS

Example 1 describes the preparation of one embodiment of the inorganic oxide catalyst support for the catalyst and process of the present invention.

EXAMPLE 1

Forty milliliters of freshly distilled anhydrous toluene were added to five grams of a dried silica gel. One milliliter of $(EtO)_3SiCH_2CH_2PPh_2$ was added under $N_2$, and the resulting mixture refluxed for 20 hours. The mixture was filtered and the solid silica gel extracted with acetone for 8 hours. The solid silica gel thereby obtained was filtered and dried under vacuum.

Example 2 describes the preparation of the inorganic oxide supported ruthenium based catalyst from the support material of Example 1.

EXAMPLE 2

The ruthenium complex precursor, $RuCl_2(AN)_3$, was prepared by refluxing $RuCl_3 \cdot 3H_2O$ and acrylonitrile in ethanol. $RuCl_2(AN)_3$, 0.3 gm, was added to one gram of the support material from Example 1 so that the total Ru/P ratio was about 3. Twenty milliliters of $Ch_2Cl_2$ was added as a solvent and the reaction mixture stirred under nitrogen for 24 hours. The catalyst was then filtered, washed with solvent until the filtrate became colorless, and dried under vacuum for 8 hours. The resulting catalyst contained 2.3 percent by weight ruthenium and had a P/Ru molar ratio of about 1:1.

Comparative Examples 3 through 11 describe a series of experiments demonstrating a dimerization process. These dimerization processes are analogous to the dimerization process and catalyst of the present invention, except that the experiments in Comparative Examples 3–11 were performed using a ruthenium catalyst which was not supported on an inorganic oxide, but was homogeneous with respect to the reaction mixture.

Unless indicated otherwise, these experiments were performed by placing 0.036 mmole of catalyst, 16 mmole of acrylonitrile, 0.7 mmole N-methylpyrrolidine, 4 of ml acetone and 0.15 ml $C_{15}H_{32}$, as an internal standard for gas chromatography, in a 45 ml autoclave. The autoclave was sealed, purged with $H_2$, pressurized with hydrogen to a pressure of 80 psi and heated to 110° C. for 3 hours. The reaction mixture was then removed from the autoclave, filtered to separate the catalyst and subjected to analysis by gas chromatography.

The low boiling fraction of the reaction mixture, containing acrylonitrile and proprionitrile, was analyzed by gas chromatography. The high boiling fraction, containing alpha-methyleneglutaronitrile, 1,4-dicyanobutenes and adiponitrile, among other things, was separately analyzed by gas chromatography.

In Table II and subsequent tables, percent ruthenium represents the weight percent of ruthenium in the ruthenium containing supported catalyst, "PN" denotes propionitrile, the heading "dimer" denotes 1,4-dicyanobutenes plus adiponitrile, and "TN" indicates the turnover number of the catalyst. Percent conversion and selectivity were calculated as follows:

$$\text{Percent Yield } PN = \frac{\text{Moles } PN}{\text{Moles } AN \text{ Fed}} \times 100$$

$$\text{Percent Yield Dimer} = \frac{2 \times \text{Moles Dimer}}{\text{Moles } AN \text{ Fed}} \times 100$$

$$\text{Percent Conversion} = \frac{\text{Moles } AN \text{ fed} - \text{moles } AN \text{ recovered}}{\text{Moles } AN \text{ fed}} \times 100$$

$$\text{Selectivity} = \frac{\text{Percent Yield Specific Product}}{\text{Percent Yield } PN + \text{Percent Yield dimer}} \times 100$$

$TN$ = Number of Dimer Molecules Produced/Number of Ru Atoms/Hours

The results of the analysis for Comparative Examples 3–11 are represented below in Table II. These results provide a basis for comparing the conversion and selectivity of the process and catalyst of the present invention, wherein the catalyst comprises an inorganic oxide catalyst support, trivalent pendant atoms covalently bonded to the support and ruthenium complexed with the trivalent pendant atoms, with catalysts and processes wherein the catalyst is homogeneous with the reaction mixture. Greater conversion could be expected using a homogeneous catalyst, rather than a heterogeneous catalyst, due to the fact that a homogeneous catalyst is more accessible to the reactants.

TABLE II

| EX. NO. | CATALYST | ADDITIVE | % CONVERSION | SELECTIVITY PN | DIMER |
|---|---|---|---|---|---|
| C3 | $RuCl_2(AN)_3$ | $CoF_3$ | 43 | 37 | 63 |
| C4 | $RuCl_2(AN)_3$ | $Co(acac)_3$ | 18 | 36 | 64 |
| C5 | $RuCl_2(AN)_3$ | $Co_3(PO_4)_2 8H_2O$ | 46 | 36 | 64 |
| C6 | $RuCl_2(AN)_3$ | $CoBr_2$ | 32 | 43 | 57 |
| C7 | $RuCl_2(AN)_3$ | $[Co(NH_3)_6]Cl_3$ | 43 | 37 | 63 |
| C8 | $RuCl_2(AN)_3$ | $Co(BF_4)_2 6H_2O$ | 38 | 41 | 59 |
| C9 | $RuCl_2(AN)_3$ | $CoTiO_3$ | 37 | 37 | 63 |
| C10 | $RuCl_2(AN)_3$ | $CuCl_2$ | 50 | 39 | 61 |
| C11 | $RuCl_2(AN)_3$ | $CoSO_4 7H_2O$ | 40 | 38 | 62 |

Examples 12 through 21 describe a series of experiments demonstrating various embodiments of the present invention wherein the catalyst comprises an inorganic oxide catalyst support, trivalent pendant atoms covalently bonded to the support and ruthenium complexed with the trivalent pendant atoms. These experiments were performed by the procedure outlined above for Comparative Examples 3–11. The results of the experiments for Examples 12–21, indicated in Table III, were analyzed by the methods described above.

TABLE III

| EX. NO. | CATALYST | ADDITIVE | % CONVERSION | SELECTIVITY PN | DIMER |
|---|---|---|---|---|---|
| 12 | $RuCl_2(AN)_3$ on Silica | None | 56 | 37 | 63 |
| 13 | $RuCl_2(AN)_3$ on Silica | $CoF_2$ | 46 | 42 | 58 |
| 14 | $RuCl_2(AN)_3$ on Silica | $Co(acac)_3$ | 28 | 40 | 60 |
| 15 | $RuCl_2(AN)_3$ on Silica | $Co_3(PO_4)_2 \cdot 8H_2O$ | 55 | 38 | 62 |
| 16 | $RuCl_2(AN)_3$ on Silica | $CoBr_2$ | 53 | 39 | 61 |
| 17 | $RuCl_2(AN)_3$ on Silica | $[Co(NH_3)_6]Cl_3$ | 50 | 36 | 64 |
| 18 | $RuCl_2(AN)_3$ on Silica | $Co(BF_4)_2 \cdot 6H_2O$ | 48 | 41 | 59 |

TABLE III-continued

| EX. NO. | CATALYST | ADDITIVE | % CON- VER- SION | SELEC- TIVITY PN | DI- MER |
|---|---|---|---|---|---|
| 19 | RuCl$_2$(AN)$_3$ on Silica | CoTiO$_3$ | 56 | 37 | 63 |
| 20 | RuCl$_2$(AN)$_3$ on Silica | CuCl$_2$ | 56 | 40 | 60 |
| 21 | RuCl$_2$(AN)$_3$ on Silica | CoSO$_4$.7H$_2$O | 46 | 39 | 61 |

A comparison of the results of Examples 12–21 with the results of Comparative Examples 3–11 shows that the conversions and selectivities obtained using the heterogeneous catalyst of the present invention are better than or within the experimental error of the conversions and selectivities obtained by the homogeneous catalyst of Examples 3–11.

Examples 22 through 26, performed by the procedure outlined above for Comparative Examples 3–11, demonstrate that while the concentration of the heterogeneous ruthenium/trivalent pendant atom/inorganic oxide catalyst in the process of the present invention may affect the conversion of the acrylic compound, the catalyst of the present invention appears consistent in its selectivity for the dimer and yields selectivities which are, at minimum, as good as or within the experimental error of ruthenium catalysts which do not comprise the heterogeneous ruthenium/trivalent pendant atom/inorganic oxide catalyst of the present invention. These results of the experiments for Examples 22–26 were analyzed by the procedure outlined above, and are reported below in Table IV.

TABLE IV

| EX. NO. | CATALYST | mmole of Catalyst | % CON- VERSION | SELECTIVITY PN | DIMER |
|---|---|---|---|---|---|
| 22 | RuCl$_2$(AN)$_3$ | 0.018 | 22 | 35 | 65 |
| 23 | " | 0.036 | 43 | 35 | 65 |
| 24 | " | 0.072 | 54 | 35 | 65 |
| 25 | " | 0.145 | 72 | 35 | 65 |
| 26 | " | 0.290 | 73 | 38 | 62 |

Examples 27 through 31, performed by the procedure outlined above for Comparative Examples 3–11, provide a basis for comparing the selectivity of the catalyst and process of the present invention with similar dimerization catalysts and processes wherein the catalyst is a ruthenium based catalyst, but does not have the inorganic oxide/trivalent pendant atom ligating system of the catalyst and process of the present invention. The results of the experiments for Examples 27–31 were analyzed by the procedures outlined above and are reported below in Table V. In this table "Silica" denotes a silica support that does not have the inorganic oxide/trivalent pendant atoms ligating system of the present invention, "Polystyrene-Ligand" denotes a polystyrene support covalently bonded to trivalent pendant atom ligating systems, and "Silica-Ligand" denotes the inorganic oxide/trivalent pendant atom ligating system of the present invention.

TABLE V

| Ex. | Support | Heat Treat- ment | AN % Conv. | % Ru | Ru/P | Selec- tivity PN % | Dimer % |
|---|---|---|---|---|---|---|---|
| 27 | Silica | 150° C. | 85 | 1.6 | — | 41 | 59 |
| 28 | Ligand-Silica | 150° C. | 82 | 2.3 | 0.96 | 40 | 60 |
| 29 | Silica | 500° C. | 53 | 1.6 | — | 39 | 61 |
| 30 | Ligand-Silica | 500° C. | 60 | 2.6 | 2.0 | 39 | 61 |
| 31 | Polystyrene- ligand | — | 23 | — | 0.8 | 38 | 62 |

Although the concentration of ruthenium differed among the experiments of Examples 27–31, the concentration of ruthenium would not be expected to affect the selectivity of these catalysts for the dimer. As Examples 27–31 show, the selectivity for the dimer of the Ligand-Silica catalyst of the present invention (e.g. Examples 28 and 30) is commensurate with the selectivity of Silica and Ligand-Polystyrene catalyst systems.

Comparative Examples 32 and 33 and Example 34 were performed to demonstrate the recycle potential of the catalyst of the present invention relative to the recycle potential of catalysts wherein ruthenium is disposed on supports which are not inorganic oxides and/or do not have the inorganic oxide/trivalent pendant atom ligating system of the present invention. These experiments were performed using the procedure outlined above for Examples 3–11. While fresh catalyst was used for the first run of each Example, the catalyst in subsequent runs was recycled from the previous run. The results of the experiments for Comparative Examples 32 and 33 and Example 34 were analyzed by the procedures outlined above and are reported below in Table VI.

TABLE VI

| Ex. | Cycle | % Ru Loss | Selectivity % Conv. | PN | Dimer | TN | Remarks |
|---|---|---|---|---|---|---|---|
| C32 | 1 | 3 | 16 | 42 | 58 | 59 | RuCl$_2$(AH)$_3$ |
|  | 2 | <3 | 2 | 58 | 42 | 6 | on 20 percent cross- |
|  | 3 | <3 | 0 | — | — | — | linked polystyrene PPh$_2$ |
| C33 | 1 | 11 | 63 | 36 | 64 | 96 | RuCl$_2$(AN)$_3$ |
|  | 2 | 4 | 32 | 37 | 63 | 54 | on silica |
|  | 3 | 2 | 24 | 38 | 62 | 42 |  |
|  | 4 | 1 | 17 | 37 | 63 | 31 |  |
| 34 | 1 | 8 | 69 | 40 | 60 | 61 | RuCl$_2$(AN)$_3$ |
|  | 2 | 2 | 33 | 41 | 59 | 31 | on silica —O— |
|  | 3 | 1 | 40 | 37 | 63 | 41 | Si—CH$_2$CH$_2$PPh$_2$ |
|  | 4 | 1 | 32 | 38 | 62 | 33 |  |

The results of Comparative Examples 32 and 33 and Example 34 clearly demonstrate the superiority of the catalyst and process of the present invention. As the results of these experiments show, the conversion of the ruthenium/trivalent pendant atom/inorganic oxide catalyst of the present invention, both in the initial run and during recycle runs, was higher than the conversion obtained in parallel experiments using the silica and ligand-polystyrene catalysts of Comparative Examples 32 and 33. The experiments also demonstrate that high conversion can be maintained using the catalyst and process of the present invention while maintaining good selectivity for the dimer.

The above Examples were performed to demonstrate the operability of the catalyst of the present invention and to demonstrate that superior leach resistance, catalyst stability, conversion of acrylic compounds and selectivity for the dimer may be obtained using the process and catalyst of the present invention. It is to be understood, however, that the invention is not to be limited by the examples. Selection of specific inorganic oxide supports, promoter ligands, solvents, reaction conditions, and ratios of ruthenium to acrylic compound can be determined by the total specification disclosure provided herein, without departing from the spirit and scope of the invention herein disclosed and described. The scope of the invention, including modifications, variations and equivalents, is to be determined by the scope of the following claims:

We claim:

1. A process for the dimerization of an acrylic compound selected from the group consisting of acrylonitrile, methacrylonitrile, acrylamide, methacrylamide, acrolein, methacrolein, acrylic acid, methacrylic acid, methyl acrylate, ethyl acrylate and methyl methacrylate, in the liquid phase comprising contacting an acrylic compound with a ruthenium based catalyst in the presence of hydrogen, at a pressure from about 1 psi to about 1500 psi and a temperature in the range of about 50° C. to about 400° C., wherein the catalyst comprises an inorganic oxide catalyst support, trivalent pendant atoms covalently bonded to the support and ruthenium complexed with the trivalent pendant atoms, wherein the ruthenium is in the form of a complex represented by the formula:

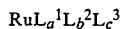

wherein $L^1$ is a mono or bidentate ligand selected from F, Cl, Br, I, 2,4-pentanedionate, or mixtures thereof, wherein $L^2$ is one or more of acetonitrile, propionitrile, benzonitrile, water and a group of the formula:

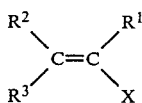

wherein X is CN, $CO_2R^4$, CHO or $CONR_2^4$ and $R^1$, $R^2$, $R^3$ and $R^4$ are independently selected from $C_{1-16}$ alkyl, $C_{6-16}$ aryl and H;
wherein $L^3$ is $R_3{}^5P$, $R_3{}^5As$, $R_3{}^5Sb$, $R_3{}^5N$, $R_3{}^5Bi$, $R_2{}^6S$ and $R_2{}^6O$, or mixtures thereof wherein each $R^5$ is a $C_{1-16}$ group independently selected from alkyl, aryl, alkoxy, aryloxy, dialkylamino and diarylamino and $R^6$ is independently selected from $C_{1-16}$ alkyl, $C_{6-16}$ aryl or H; and
wherein
a is 0 to 3;
b is 0 to 6;
c is 0 to 6; and
a+b+c is at least 2; and
wherein $L^1$, $L^2$ and $L^3$ are additively bonded to the Ru with 4 to 6 ligating bonds.

2. The process of claim 1 wherein the inorganic oxide is selected from the group consisting of $Li_2O$, $Cs_2O$, BeO, $MgO_2$, $CaO_2$, $BaO_2$, $Y_2O_3$, $TiO_2$, $ZrO_2$, $HfO_2$, $NbO_2$, $Ta_2O_5$, $WO_2$, ZnO, CdO, $Al_2O_3$, $Ga_2O_3$, $In_2O_3$, $Tl_2O_3$, $SiO_2$, $GeO_2$, $SnO_2$, $PbO$, $Pb_2O_3$, $As_2O_5$, $CeO_2$, $Ce_2O_3$ and $ThO_2$ and mixtures thereof.

3. The process of claim 1 wherein the inorganic oxide is selected from the group consisting of $Li_2O$, $Cs_2O$, BeO, $MgO_2$, $CaO_2$, $BaO_2$, $Al_2O_3$, $Ga_2O_3$, $In_2O_3$, $Tl_2O_3$, $SiO_2$, $GeO_2$, $SnO_2$, $PbO$, $Pb_2O_3$, $TiO_2$, $ZrO_2$, $HfO_2$, $NbO_2$ and $Ta_2O_5$ and mixtures thereof.

4. The process of claim 2 wherein the inorganic oxide is selected from the group consisting of $Al_2O_3$, $Ga_2O_3$, $In_2O_3$, $Tl_2O_3$, $SiO_2$, $GeO_2$, $SnO_2$, $PbO$, $Pb_2O_3$, $TiO_2$, $ZrO_2$, $HfO_2$, $Y_2O_3$ and mixtures thereof.

5. The process of claim 4 wherein the inorganic oxide is selected from the group consisting of $Al_2O_3$, $Ga_2O_3$, $In_2O_3$, $Tl_2O_3$, $SiO_2$, $GeO_2$, $SnO_2$, $PbO$ and $Pb_2O_3$ and mixtures thereof.

6. The process of claim 1 wherein the inorganic oxide is selected from $SiO_2$, $TiO_2$ and $Al_2O_3$ and mixtures thereof.

7. The process of claim 1 wherein the trivalent pendant atoms are selected from the group consisting of P, As, Sb, Bi and N.

8. The process of claim 7 wherein the pendant atoms are phosphorus.

9. The process of claim 1 wherein the acrylic compound is selected from the group consisting of acrylonitrile, methacrylonitrile, acrolein, methacrolein, methyl acrylate, methyl methacrylate, acrylic acid, methacrylic acid and acrylamide.

10. The process of claim 9 wherein the acrylic compound is acrylonitrile.

11. The process of claim 1 wherein the acrylic compound is contacted with the catalyst in the presence of a solvent which is selected from the group consisting of ketones, alcohols, alkyl substituted aromatics, unsubstituted aromatics, ethers, organic nitriles and mixtures thereof.

12. The process of claim 1 wherein the acrylic compound is contacted with the catalyst in the absence of a solvent.

13. The process of claim 1 wherein the catalyst comprises about 0.1 to about 10 weight percent ruthenium.

14. The process of claim 13 wherein the catalyst comprises about 0.3 to about 3 weight percent ruthenium.

15. The process of claim 1 wherein the molar ratio of trivalent pendant atoms to the ruthenium is equal to or less than 20:1.

16. The process of claim 15 wherein the molar ratio of trivalent pendant atoms to the ruthenium is about 10:1 to about 1:1.

17. The process of claim 1 wherein the molar ratio of ruthenium to the acrylic compound is about $10^{-4}$:1 to about 1:1.

18. The process of claim 17 wherein the molar ratio of ruthenium to the acrylic compound is about $4\times10^{-4}$:1 to about $2\times10^{-3}$:1.

19. The process of claim 1 wherein the temperature is about 60°–200° C.

20. The process of claim 19 wherein the temperature is about 80°–150° C.

21. The process of claim 1 wherein the acrylic compound is contacted with the catalyst at a pressure of about 10–800 psi.

22. The process of claim 21 wherein the acrylic compound is contacted with the catalyst at a pressure of about 60–400 psi.

* * * * *